United States Patent
Gao et al.

(10) Patent No.: US 11,779,525 B2
(45) Date of Patent: Oct. 10, 2023

(54) PROCESS AND COSMETIC COMPOSITION FOR GLOSS AND BLUR

(71) Applicant: CONOPCO, INC., Trumbull, CT (US)

(72) Inventors: Huailing Gao, Hefei (CN); Zhao Pan, Hefei (CN); Lin Wang, Shanghai (CN); Shuhong Yu, Hefei (CN); Shuqi Zhu, Shanghai (CN)

(73) Assignee: CONOPCO, INC., Englewood Cliffs, NJ (US)

( * ) Notice: Subject to any disclaimer, the term of this patent is extended or adjusted under 35 U.S.C. 154(b) by 308 days.

(21) Appl. No.: 17/295,620

(22) PCT Filed: Dec. 9, 2019

(86) PCT No.: PCT/EP2019/084230
§ 371 (c)(1),
(2) Date: May 20, 2021

(87) PCT Pub. No.: WO2020/136001
PCT Pub. Date: Jul. 2, 2020

(65) Prior Publication Data
US 2022/0015994 A1    Jan. 20, 2022

(30) Foreign Application Priority Data

Jan. 28, 2019    (EP) .................................... 19153862

(51) Int. Cl.
*A61K 8/25*    (2006.01)
*A61K 8/02*    (2006.01)
*A61K 8/58*    (2006.01)
*A61K 8/96*    (2006.01)
*A61Q 1/12*    (2006.01)

(52) U.S. Cl.
CPC ............ *A61K 8/0254* (2013.01); *A61K 8/025* (2013.01); *A61K 8/585* (2013.01); *A61K 8/965* (2013.01); *A61Q 1/12* (2013.01); *A61K 2800/26* (2013.01); *A61K 2800/412* (2013.01); *A61K 2800/621* (2013.01)

(58) Field of Classification Search
CPC ....................................................... A61K 8/25
See application file for complete search history.

(56) References Cited

U.S. PATENT DOCUMENTS

| | | |
|---|---|---|
| 6,432,535 B1 | 8/2002 | Noguchi et al. |
| 2002/0011186 A1 | 1/2002 | Tanaka et al. |
| 2002/0157574 A1 | 10/2002 | Weitzel et al. |
| 2005/0158257 A1 | 7/2005 | Ogawa et al. |
| 2005/0163730 A1 | 7/2005 | Rosevear et al. |
| 2007/0172438 A1 | 7/2007 | Kruger et al. |
| 2011/0086076 A1 | 4/2011 | Mousset et al. |
| 2011/0123580 A1 | 5/2011 | Touyama et al. |
| 2013/0164356 A1 | 6/2013 | Pfaff et al. |
| 2015/0209260 A1 | 7/2015 | Sayer et al. |
| 2017/0290750 A1 | 10/2017 | Hamm et al. |
| 2018/0344586 A1 | 12/2018 | Rohrer et al. |

FOREIGN PATENT DOCUMENTS

| | | | |
|---|---|---|---|
| CN | 105632885 A | * | 6/2016 |
| EP | 1329483 | | 7/2003 |
| JP | H09235217 | | 9/1997 |
| JP | 2001279126 | | 10/2001 |
| JP | 2002241226 | | 8/2002 |
| WO | WO2017127362 | | 7/2017 |
| WO | WO2017220310 | | 12/2017 |

OTHER PUBLICATIONS

Search Report and Written Opinion in EP19153862; dated Jul. 16, 2019; European Patent Office (EPO).
EMD; Works of art begin with the right materials Ingredients for cosmetics; Rona; Oct. 1, 2010; pp. 1-20; XP055601134; Retrieved from the Internet: URL:https://www.emdmillipore.com.
Dr. Ralf Emmert; Quantification of the Soft-Focus Effect; Cosmetics & Toiletries magazine; Jul. 1, 1996; pp. 57-61; XP009029669; vol. 111; No. 7; Allured Publishing Corp.; United States of America.
BASF; Effect pigments for cosmetics and personal care; Colors & Effects; Jul. 1, 2017; pp. 1-15; XP055601931; Retrieved from the internet: URL:https://www.basf.com/us/en/products/General-Business-Topics/pigments/Products/Pigments-for-cosmetics.html.
Sensient Cosmetic Technologies; Matlake OPA; Technical Data Sheet; Mar. 6, 2017; pp. 1-1; XP055601789; Retrieved from the Internet: URL:https//www.ulprospector.com/documents/1180670.pdf?bs=818&b=235872&st=20&r=eu&ind=personalcare.

(Continued)

*Primary Examiner* — Benjamin J Packard
(74) *Attorney, Agent, or Firm* — Stephanie Huang

(57) ABSTRACT

Disclosed a method of preparing composite particles comprising a non-porous spherical particulate inorganic material deposited on a plate-like inorganic material, where refractive index of said particulate inorganic material is greater than that of said plate-like inorganic particulate material, wherein, said spherical material occupies 20 to 80% of total surface area of said plate-like material and wherein the amount of said spherical material accounts for 2 to 20 wt % of said composite particles, further wherein said plate-like inorganic material is mica and said non-porous spherical particulate inorganic material is silicone dioxide, said method comprising the steps of: (iv) silanization of said plate-like inorganic material to get a silanized material having functional groups "A"; (v) silanization of said non-porous spherical particulate inorganic material to get a silanized material having functional groups "B", where A≠B; and where said "A" and said "B" are capable of reacting with each other such that by way of their reaction, said non-porous spherical particulate inorganic material deposits on said plate-like inorganic material; and, (vi) reacting said silanized material having functional groups "A" with said silanized material having functional groups "B".

15 Claims, No Drawings

(56) References Cited

OTHER PUBLICATIONS

Search Report and Written Opinion in PCTEP2019084230; dated Feb. 5, 2020; World Intellectual Property Org. (WIPO).
IPRP1 in PCTEP2019084230; dated Jul. 8, 2021; World Intellectual Property Org. (WIPO).
Shunchao Gu et al.; Preparation and colloidal stability of monodisperse magnetic polymer particles; Journal of Colloid and Interface Science ; May 12, 2005; pp. 419-426; vol. 289; Elsevier, Inc.
Akira Matsubara; Skin translucency: what is it and how is it measured?; IFSCC Congress 2006 Osaka, Japan; 2006; pp. 1-7.

\* cited by examiner

PROCESS AND COSMETIC COMPOSITION FOR GLOSS AND BLUR

CROSS REFERENCE TO RELATED APPLICATIONS

The present application is a U.S. National Phase Application under 35 U.S.C. § 371 of International Application No. PCT/EP2019/084230, filed on Dec. 9, 2019, which claims priority to International Application No. PCT/CN2018/124886, filed on Dec. 28, 2018 and European Patent Application No. 19153862.8, filed on Jan. 28, 2019, the contents of which are incorporated herein in their entireties.

FIELD OF THE INVENTION

The present invention relates to a material obtainable by a novel process for use in cosmetic compositions. More particularly, the invention relates to a material obtainable by a novel process for use in compositions for blurring or hiding superficial or surface imperfections of skin, such as fine lines and wrinkles by creating optical effects on the skin.

BACKGROUND OF THE INVENTION

Our skin is amenable to deterioration due to dermatological disorders, environmental factors such as strong sunlight and due to the normal aging process (chrono-ageing), which may be accelerated by exposure to sun (photo-ageing). In recent years the demand for cosmetic compositions and cosmetic methods for improving the appearance of skin has grown enormously. Consumers are increasingly seeking cosmetic compositions to treat, delay or conceal the visible signs of chrono-ageing and photo-ageing skin such as wrinkles, fine lines, sagging, hyperpigmentation and age spots.

Imperfect skin can be hidden in two ways through manipulation of transmission of light. In the first manner, one or more ingredients of the cosmetic composition may simply reflect light. Usually, the scientists who formulate cosmetic compositions prefer to rely on talc, silica, kaolin and other inorganic particulate materials which have high refractive indices. An alternative approach is referred to as achieving a soft-focus effect, also called blurring effect. In this case, the incident light is distorted by scattering (lensing) and certain ingredients could be used to create such an effect. Such ingredients operate as lenses which bend and twist the light in multiple directions. An example of the above is particulate silicone elastomers.

Soft focus or blurring is a technique which can be used to hide or conceal superficial or surface imperfections of the skin. Incoming light is distorted by scattering (lensing). When particulate components operate as lenses to bend and twist light in many directions, incoming light is distorted by scattering (lensing). In such compositions, the ingredient or ingredients of the cosmetic, operate as lenses to bend and twist light in multiple directions. Wrinkles and fine lines are perceivable primarily as dark, non-reflective areas because of the way light falls and remains there. In contrast if light is reflected and diffused, the wrinkles become less visible. Methods have been developed to project light into the wrinkles and immediately eliminate the dark areas that make the crease obvious. The 'soft focus effect' was described by Dr. Emmert in "Quantification of the Soft-Focus Effect", Cosmetics and Toiletries, Vol. 111, 57-61 (1996).

Where transmission of light is insufficiently hindered, the opposite may occur. Here the glow may be healthy but aesthetically displeasing skin topography and color may now be apparent. The micro-texture of the skin influences how light reflects because surface curvatures change the angle of incidence of light. Such changes in the angle of incidence determine whether the light reflected to a particular position (of observation) is specular light or diffuse light, i.e., it has first interacted with the skin before being reflected.

While it is desirable to hide imperfect skin through a matte effect, there is also a desire to achieve a healthy skin radiance. A cosmetic which is too opaque hides the skin under a paint-like coating. Some refer to this as whitening.

It is known that by use of certain particulate materials it is possible to hide or conceal the superficial imperfections. However, if more of such particles are included in the cosmetic compositions, the particles begin to affect the gloss or shine. Therefore, it is a technical problem to balance the desirable gloss of skin while at the same time striving to conceal or hide the surface imperfections of the skin while using relatively less amount of particulate material.

WO2017220310 A1 (Unilever) discloses a personal care composition comprising retinol, porous silica, silicone elastomer. The composition is useful for soft focus.

In the publication mentioned immediately hereinabove, an index called as L&W Index is used to compare efficacy of a given cosmetic composition vis-a-vis others. The Index is directly proportional to performance.

US20130164356 A1 (Merck) discloses that an object of the invention is to find effect pigments which have high color saturation a high hiding power without losing their optical properties, e.g., luster and color purity. Effect pigments based on flake-form substrates which have a roundish shape are found to increase color saturation and an increased hiding power compared with effect pigments from the prior art based on substrates having an oblong shape with greater edge roughness. This application discloses effect pigments based on flake-form substrates, where the substrates have a circular form factor (circumference$^2$/area standardized to a circle) of 1.2 to 2, and are coated with at least one high-refractive-index layer having a refractive index of 1.8.

US2002011186A (JGC) discloses flaky fine powder comprising a flaky substance as the base and silica particles covering the surface of the base to reduce glossiness of the base caused by irregular reflection of light on its surface and improving the slipperiness. The powder comprises a flaky base substance such as natural mica and silica particles deposited on the base surface, wherein the silica particles may be optionally further immobilized by the hydrolysate of alkoxysilane or silica gel. The flaky fine powder is produced either by adding alkoxysilane to a dispersion containing a flaky substance and silica particles and hydrolyzing it, by adding a silicic acid solution to the dispersion and gelling it, or by adding a combination of alkoxysilane and silicic acid solution. This powder can be compounded with various ingredients and is useful in cosmetics.

U.S. Pat. No. 6,432,535 BA (Merck) discloses a composite material in which thin flakes of a plate-like pigment contain particles of spherical silica having an average particle size of 20 to 400 nm on the surface of the flaky substrate having an average particle size of 0.5 to 10 μm and then the spherical silica is further coated with ultrafine particles of titanium dioxide. The composite particles are good for soft focus effects, spreading, UV protection and whiteness.

US2002011186 A (Merck) discloses flaky fine powder comprising a flaky substance as the base and silica particles covering the surface of the base. The particles are useful to reduce the glossiness of the base caused by the irregular reflection of light on its surface and improving slipperiness. The flaky fine powder is produced either by adding alkoxysilane to a dispersion containing a flaky substance and silica particles and hydrolyzing it, by adding a silicic acid solution to the dispersion and gelling it, or by adding a combination of alkoxysilane and silicic acid solution. The particles are less prone to agglomerate.

SUMMARY OF THE INVENTION

It is known that certain particulate materials can hide or conceal superficial imperfections of skin such as fine lines and wrinkles. However, as the amount or dosage of such particles is increased, they begin to adversely affect the gloss or shine of skin.

The composite particles obtainable by the novel process in accordance with this invention comprise a non-porous spherical particulate inorganic material deposited on a plate-like inorganic material. The particles are suited for use in cosmetic compositions to get an optimum balance between gloss and blur or blurring, which are two optical effects. The inventors believe that such a balance of optical properties is possible due to the controlled amount of non-porous spherical particulate inorganic material, such as silica, and because the spherical material occupies from 20 to 80% of the total surface area of the plate-like material.

The material according to this invention, i.e., composite particles, comprise a non-porous spherical particulate inorganic material deposited on a plate-like inorganic material. The refractive index of the spherical particulate inorganic material is more than that of the plate-like inorganic material. The spherical material occupies a certain defined surface area of the plate-like particles and the amount of said spherical material is properly balanced to optimize the in-use performance of the particles.

In accordance with a first aspect is disclosed a method of preparing composite particles comprising a non-porous spherical particulate inorganic material deposited on a plate-like inorganic material, where refractive index of said particulate inorganic material is greater than that of said plate-like inorganic particulate material, wherein, said spherical material occupies 20 to 80% of total surface area of said plate-like material and wherein the amount of said spherical material accounts for 2 to 20 wt % of said composite particles, further wherein said plate-like inorganic material is mica and said non-porous spherical particulate inorganic material is silicone dioxide, said method comprising the steps of:
(i) silanization of said plate-like inorganic material to get a silanized material having functional groups "A";
(ii) silanization of said non-porous spherical particulate inorganic material to get a silanized material having functional groups "B", where A≠B; and where said "A" and said "B" are capable of reacting with each other such that by way of their reaction, said non-porous spherical particulate inorganic material deposits on said plate-like inorganic material; and,
(iii) reacting said silanized material having functional groups "A" with said silanized material having functional groups "B".

All other aspects of the present invention will more readily become apparent upon considering the detailed description and examples which follow.

In accordance with a second aspect is disclosed a cosmetic composition comprising the composite particles obtainable by the process of the first aspect.

In accordance with a third aspect is disclosed use of the composite particles obtainable by the process of the first aspect in a cosmetic composition for enhancing gloss of skin.

In accordance with a fourth aspect is disclosed use of the composite particles obtainable by the process of the first aspect in a cosmetic composition for hiding superficial imperfections of skin.

In accordance with a fifth aspect is disclosed a method of enhancing gloss of skin comprising a step of applying thereto a cosmetic composition comprising the composite particles obtainable by the process of the first aspect of the invention.

In accordance with a sixth aspect is disclosed a cosmetic method of hiding superficial imperfections of skin comprising a step of applying thereto a cosmetic composition comprising the composite particles obtainable by the process of the first aspect of the invention.

DEFINITIONS

"Skin" as used herein, is meant to include skin on the face, neck, scalp, underarms, chest, back, arms, hands, legs, scalp, feet, buttocks and abdomen, preferably the hands, neck, face, and underarms.

Superficial imperfections of skin means and include blemishes (age spots, blotches), pores, fine lines and wrinkles, and grooves (the words "lines," "wrinkles," and grooves being used interchangeably herein). "Age spots" as used herein means any hyperpigmentation (e.g. including solar lentigo), spots and/or freckles.

The term treating or treatment as used herein includes within its scope reducing, delaying and/or preventing the abovementioned skin conditions and generally enhancing the quality of skin and improving its appearance and texture.

By "specular reflectance" is meant mirror-like reflection of light from a surface in which light from a single incoming source is reflected into a single outgoing direction. The light may be of any wavelength able to undergo specular reflectance from the surface of facial skin, preferably it is visible light.

By "a cosmetic composition" as used herein, is meant to include a composition for topical application to the skin of mammals, especially human beings. Such a composition may be generally classified as leave-on or rinse off but is preferably of the leave-on type. The composition is formulated into a product which is applied to a human body specifically for improving appearance. The composition of the present invention can be in the form of a liquid, lotion, cream, foam, scrub, gel, or toner, or applied with an implement or via a face mask or a pad. Non-limiting examples of such compositions include leave-on skin lotions, creams, foundations, sunless tanners and sunscreen lotions.

Refractive index values referred to herein are determined at 25° C. and wavelength of 589 nm.

Where primary particle size is mentioned this means the size (diameter) measurable by transmission electron microscopy (TEM) using a method such as that described by S. Gu et al in *Journal of Colloid and Interface Science,* 289 (2005) pp. 419-426.

Except in the examples, or where otherwise explicitly indicated, all numbers in this description indicating amounts of material or conditions of reaction, physical properties of materials and/or use may optionally be understood as modified by the word "about". All amounts are by weight of the final composition, unless otherwise specified. The term "solid" as used herein means that the material is not fluid at 25° C. It should be noted that in specifying any range of values, a given upper value can be associated with any lower value. For the avoidance of doubt, the word "comprising" is intended to mean "including" but not necessarily "consisting of" or "composed of". In other words, the listed steps or options need not be exhaustive. The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

DETAILED DESCRIPTION

The Composite Particles

Composite particles as obtainable by the process of the invention comprise a non-porous spherical particulate inorganic material deposited on a plate-like inorganic material. In other words, the non-porous spherical particulate inorganic material is adhered on a plate-like inorganic material.

The refractive index of the particulate inorganic material is greater than that of said plate-like inorganic particulate material.

Preferably the plate-like inorganic material is mica, talc, montmorillonite, kaolin, graphite, flake-form iron oxide, glass flake, sericite, plate-like silica, graphene, plate-like aluminum oxide, fumed alumina, aluminum oxide hydrate, aluminum hydroxide and aluminum-deposited film, barium sulfate, bismuth oxychloride, boehmite, calcium aluminum borosilicate, calcium carbonate, clay, collagen, colloidal silica, corundum, diatoms, diatomite, diatomaceous earth, gibbsite, guanine, graphite, hexagonal boron nitride, magnesium silicate, micaceous iron oxide, pyrophyllite or interference mica such as Timica FR530, Timica V or Soft Luster White.

This material will generally have an average particle size D50 ranging from about 10,000 to about 30,000 nm. For plate-like materials the average particle size is a number average value. The platelets are assumed to have a circular shape with the diameter of the circular surface averaged over many particles. The thickness of the plate-like particles is considered to be a separate parameter. For instance, the plate-like material or platelets can have an average particle size of 35,000 nm and an average thickness of 400 nm. For purposes herein, thickness is considered to range from about 100 to about 600 nm. Laser light scattering can be utilized for measurement except that light scattered data has to be mathematically corrected from the spherical to the non-spherical shape. Optical and electron microscopy may be used to determine average particle size. Thickness is normally only determined via optical or electron microscopy.

It is preferred that the refractive index of this material is at least about 1.8, generally from about 1.9 to about 4, more preferably from about 2 to about 3, optimally between about 2.5 and 2.8.

Size of the plate-like material may also be important because smaller particles reflect too little light to be readily apparent, while larger particles would be visible as discrete objects and thereby provide too much glitter or reflectance. The reflectance (index of refraction) of the platy crystal cannot be too high. Too high of an index of refraction will inhibit the transmission of natural skin color and create a cosmetic sheen. With too low an index of refraction, the particles will have approximately the same index of refraction as the skin or the product film, resulting in a weak reflectance, thereby diminishing the appearance of radiance.

Illustrative but not limiting examples of light reflecting particles are bismuth oxychloride (single crystal platelets) and titanium dioxide coated mica. Suitable bismuth oxychloride crystals are available from EM Industries, Inc. under the trademarks Biron®NLY-L-2X CO and Biron®Silver CO (wherein the platelets are dispersed in castor oil); Biron®Liquid Silver (wherein the particles are dispersed in a stearate ester); and Nailsyn®IGO, Nailsyn®II C2X and Nailsyn®II Platinum 25 (wherein the platelets are dispersed in nitrocellulose). Most preferred is a system where bismuth oxychloride is dispersed in a $C_2$-$C_{40}$ alkyl ester such as in Biron®Liquid Silver.

Among the suitable titanium dioxide coated mica platelets are materials available from EM Industries, Inc. These include Timiron®MP-10 (particle size range 10,000-30,000 nm), Timiron®MP-14 (particle size range 5,000-30,000 nm), Timiron®MP-30 (particle size range 2,000-20,000 nm), Timiron®MP-101 (particle size range 5,000-45,000 nm), Timiron®MP-111 (particle size range 5,000-40,000 nm), Timiron®MP-1001 (particle size range 5,000-20,000 nm), Timiron®MP-155 (particle size range 10,000-40,000 nm), Timiron®MP-175 (particle size range 10,000-40,000), Timiron®MP-115 (particle size range 10,000-40,000 nm), and Timiron®MP-127 (particle size range 10,000-40,000 nm). Most preferred is Timiron®MP-111. The weight ratio of titanium dioxide coating to the mica platelet may range from about 1:10 to about 5:1, preferably from about 1:1 to about 1:6, more preferably from about 1:3 to about 1:4 by weight. Advantageously the preferred compositions will generally be substantially free of titanium dioxide outside of that required for coating mica.

Suitable coatings for mica other than titanium dioxide may also achieve the appropriate optical properties required for the present invention. These types of coated micas must also meet the refractive index of at least about 1.8. Other coatings include silica on the mica platelets.

Preferably the non-porous spherical particulate inorganic material is aluminum oxide, bismuth oxide, cerium oxide, chromium oxide, iron (II) oxide, iron (II, III) oxide, iron (III) oxide, magnesium silicate, silicon dioxide, titanium dioxide, zinc oxide, zirconium oxide, and mixtures or alloys thereof. Silicon dioxide is also referred to, in the alternative, as silica.

To be able to have an optimum effect in this sense, the diameter of the spherical material is preferably smaller than the plate-like material. Since platelet-like materials having a maximum diameter of about 1 to 500 µm are particularly suitable, spherical materials having a diameter in the range from about 0.05 to 50 µm are preferred. It is preferred that particle size of the non-porous spherical particulate inorganic material is 50 to 1000 nm.

Spherical particles based on $SiO_2$ in a particle size range of about 3 to 15 µm are known, for example, as materials for high pressure liquid chromatography and are marketed, for example, as LiChrospher® by E. Merck, Darmstadt. Preferably, the plate-like material has a diameter of about 10 to 20 times greater than the diameter of the spherical particles.

However, even more finely divided materials are particularly preferably employed, especially materials having a particle size in the range from about 0.05 to 1 µm. Such particles are preferably employed in monodisperse form, that is to say; with a particle size as uniform as possible. A commercial source for mono-disperse $TiO_2$ is the Istituto Guido Donegani, Novara, Italy.

It is particularly preferred that when the non-porous spherical particulate inorganic material is silica, the plate-like inorganic material is mica.

According to the invention, the spherical material occupies from 20 to 80% of the total surface area of the plate-like material, more preferably from 25 to 80%.

Further according to the invention the amount of the spherical material accounts for 2 to 20 wt % of the composite particles. It is preferred that the balance is the plate-like material.

Further preferably the non-porous spherical particulate inorganic material is deposited as a monolayer on the plate-like inorganic material.

It is possible to manipulate or adjust the coverage by controlling the by feed ratio between the non-porous spherical particulate inorganic material and the plate-like inorganic material during the process of synthesis of the composite. The blurring effect can be increased and gloss can be decreased by increasing this coverage.

Known technology widely used for creating a blurring effect or a soft-focus is based on particulate silicone elastomers, silica or other conventional blurring particles. Such particles do result in a matte feel. However, if it is desired to increase or enhance the blurring effect, is achieved with traditional blurring particles, the appearance is dull without shine, because the incident light is mainly diffused by particles. However, if the shine is increased by adding oil or mica, which can increase specular reflectance, it will likely affect the blur effect.

Some commercially available composite materials have randomized amount of e.g., silica coated on mica, by inducing some coupling agents like silanes or titanates, silica spheres could be coated on mica, while some form aggregates on or out of mica surface. However, high coverage composites, like the ones disclosed and claimed in the present invention, could not be achieved unless excessive silica spheres were used in synthesis.

The Method of Synthesis

In accordance with the invention there is disclosed a method of preparing composite particles comprising a non-porous spherical particulate inorganic material deposited on a plate-like inorganic material, where refractive index of said particulate inorganic material is greater than that of said plate-like inorganic particulate material, wherein, said spherical material occupies 20 to 80% of total surface area of said plate-like material and wherein the amount of said spherical material accounts for 2 to 20 wt % of said composite particles, further wherein said plate-like inorganic material is mica and said non-porous spherical particulate inorganic material is silicone dioxide, said method comprising the steps of:
(i) silanization of said plate-like inorganic material to get a silanized material having functional groups "A";
(ii) silanization of said non-porous spherical particulate inorganic material to get a silanized material having functional groups "B", where A≠B; and where said "A" and said "B" are capable of reacting with each other such that by way of their reaction, said non-porous spherical particulate inorganic material deposits on said plate-like inorganic material; and,
(iii) reacting said silanized material having functional groups "A" with said silanized material having functional groups "B".

It is preferred that the plate-like inorganic material is mica. It is further preferred that the non-porous spherical particulate inorganic material is silicon dioxide.

Preferably the mica is silanized by first reacting with (3-Aminopropyl) triethoxysilane (APTES) in an alcoholic medium to get an amine-modified mica followed by reacting the amine-modified mica with succinic anhydride in dimethylformamide medium to get the silanized material having functional groups "A", where A is carboxylic acid groups. Further preferably the silica is silanized by reacting with (3-Aminopropyl) triethoxysilane (APTES) in an alcoholic medium to get the silanized material having functional groups "B", where B is amino groups. Then the silanized material having functional groups "A" is reacted with the silanized material having functional groups "B" in the presence of (1-(3-dimethylaminopropyl)-3-ethylcarbodiimide) [EDC] and N-hydroxysuccinimide [NHS].

Cosmetic Compositions of the Invention

In accordance with another aspect is disclosed a cosmetic composition comprising composite particles of the first aspect of the invention. Preferably the composition comprises 0.2 to 10 wt %, more preferably 0.5 to 5 wt % and most preferably 0.5 to 4 wt % of the composite particles.

It is preferred that the composition additionally comprises one or more of the following ingredients.

"Silicone elastomer" as used herein refers to deformable organopolysiloxane with viscoelastic properties. Preferably the cosmetic composition comprises a silicone elastomer.

It is preferred that the silicone elastomer is cross-linked. The silicone elastomer can be obtained from curable organopolysiloxanes. Examples in this respect are: addition reaction-curing organopolysiloxane compositions which cure under platinum metal catalysis by the addition reaction between SiH-containing diorganopolysiloxane and organopolysiloxane having silicon-bonded vinyl groups; condensation-curing organopolysiloxane compositions which cure in the presence of an organotin compound by a dehydrogenation reaction between hydroxyl terminated diorganopolysiloxane and SiH-containing diorganopolysiloxane; condensation-curing organopolysiloxane compositions which cure in the presence of an organotin compound or a titanate ester, by a condensation reaction between a hydroxyl terminated diorganopolysiloxane and a hydrolyzable organosilane (this condensation reaction is exemplified by dehydration, alcohol-liberating, oxime-liberating, amine-liberating, amide-liberating, carboxyl-liberating, and ketone-liberating reactions); peroxide-curing organopolysiloxane compositions which thermally cure in the presence of an organoperoxide catalyst; and organopolysiloxane compositions which are cured by high-energy radiation, such as by gamma-rays, ultraviolet radiation or electron beams. The silicone elastomer is preferably obtained by addition reaction-curing organopolysiloxane compositions which cure under platinum metal catalysis by the addition reaction between SiH-containing diorganopolysiloxane and organopolysiloxane having silicon-bonded vinyl groups The silicone elastomer may either be an emulsifying or non-emulsifying cross-linked silicone elastomer or a combination thereof but preferably the silicone elastomer is non-emulsifying. The term "non-emulsifying," as used herein, defines cross-linked silicone elastomer from which poly-oxyalkylene units are absent. The term "emulsifying," as used herein, means cross-linked organo-polysiloxane elastomer having at least one poly-oxyalkylene (e.g., poly-oxyethylene or poly-oxypropylene) unit.

Preferred silicone elastomers are organo-polysiloxanes available under the INCI names of dimethicone/vinyl dimethicone crosspolymer, dimethicone crosspolymer and Polysilicone-11. More preferably the silicone elastomer is dimethicone/vinyl dimethicone crosspolymer.

A commonly available and suitable elastomer is DC9509 (63% solids content) Dimethicone/Vinyl dimethicone Crosspolymer (and) C12-14 Pareth-12. DOW CORNING 9509 Silicone Elastomer Suspension is a 63% nonionic suspension of the spherical silicone elastomer powder in water.

Preferably, the cosmetic compositions of the invention comprise 0.1 to 10 wt % of the silicone elastomer, more preferably 0.5 to 8 wt %, even more preferably 1 to 5 wt %.

Preferably the carrier comprises silicones which are not elastomers.

Silicones may be divided into the volatile and nonvolatile variety. Volatile silicone oils (if used) are preferably chosen from cyclic (cyclomethicone) or linear polydimethylsiloxanes containing from 3 to 9, preferably from 4 to 5, silicon atoms.

Specific examples of non-silicone emollients include stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rape seed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate, and mixtures thereof.

Of particular use also are the $C_{12-15}$ alkyl benzoate esters sold under the Finsolve® brand.

Alternatively the carrier comprises 1 to 25 wt % fatty acid or 0.1 to 80 wt % soap by weight of the composition. Mixtures of fatty acid and soap are also suitable e.g., forming a vanishing cream base which lends a matte feel to the skin. $C_{12-20}$ fatty acids are especially preferred, more preferred being $C_{14-18}$ fatty acids. The most preferred fatty acid is stearic acid, myristic acid or a mixture thereof. When present, the composition comprises 5 to 20 wt % of the fatty acids or soap. Soaps in the hydrophobic material can include alkali metal salt of fatty acids, like sodium or potassium salts, most preferred being potassium stearate. Generally a vanishing cream base in cosmetic compositions is prepared by taking a desired amount of total fatty matter and mixing with potassium hydroxide in desired amounts. The soap is usually formed in-situ during the mixing.

Preferably the carrier comprises water. Amounts of water may, for example, range from 1 to 85 wt %, more preferably from 5 to 90%, even more preferably from 35 to 80%, optimally between 40 and 70% by weight of the cosmetic composition, depending on the nature of the composition.

Further preferably the compositions of the invention comprise a skin lightening agent. The skin lightening agent is preferably chosen from one or more of a vitamin B3 compound or its derivative e.g. niacin, nicotinic acid or niacinamide or other well-known skin lightening agents e.g. adapalene, aloe extract, ammonium lactate, anethole derivatives, apple extract, arbutin, azelaic acid, kojic acid, bamboo extract, bearberry extract, bletilla tuber, bupleurum falcatum extract, burnet extract, butyl hydroxy anisole, butyl hydroxy toluene, citrate esters, Chuanxiong, Dang-Gui, deoxyarbutin, 1,3-diphenyl propane derivatives, 2,5-dihydroxybenzoic acid and its derivatives, 2-(4-acetoxyphenyl)-1,3-dithane, 2-(4-hydroxyphenyl)-1,3-dithane, ellagic acid, escinol, estragole derivatives, Fadeout (Pentapharm), Fangfeng, fennel extract, ganoderma extract, gaoben, Gatuline Whitening (Gattlefosse), genistic acid and its derivatives, glabridin and its derivatives, gluco pyranosyl-1-ascorbate, gluconic acid, glycolic acid, green tea extract, 4-hydroxy-5-methyl-3[2H]-furanone, hydroquinone, 4-hydroxyanisole and its derivatives, 4-hydroxy benzoic acid derivatives, hydroxycaprylic acid, inositol ascorbate, lemon extract, linoleic acid, magnesium ascorbyl phosphate, Melawhite (Pentapharm), *Morus alba* extract, mulberry root extract, 5-octanoyl salicylic acid, parsley extract, *Phellinus linteus* extract, pyrogallol derivatives, 2,4-resorcinol derivatives, 3,5-resorcinol derivatives, rose fruit extract, salicylic acid, Song-Yi extract, 3,4,5-trihydroxybenzyl derivatives, tranexamic acid, vitamins like vitamin B6, vitamin B12, vitamin C, vitamin A, dicarboxylic acids, resorcinol derivatives, extracts from plants viz. rubia and symplocos, hydroxycarboxylic acids like lactic acid and their salts e.g. sodium lactate, and mixtures thereof. Vitamin B3 compound or its derivative e.g. niacin, nicotinic acid or niacinamide are the more preferred skin lightening agent as per the invention, most preferred being niacinamide. Niacinamide, when used, is preferably 0.1 to 10 wt %, more preferably 0.2 to 5 wt %.

Other materials which can be included in the cosmetically acceptable carrier include humectants, thickeners and powders.

The composition can be formulated in any known format, more preferred formats being creams and lotions. The cosmetic compositions of the invention may further comprise other ingredients which are common in the art to enhance physical properties and performances. Suitable ingredients include but are not limited to binders, colorants and pigments, pH adjusting agents, preservatives, optics, perfumes, viscosity modifiers, biological additives, buffering agents, conditioners, natural extracts, essential oils and skin benefit agents including anti-inflammatory agents, cooling agents, antiperspirant agents, anti-aging agents, anti-acne agents, anti-microbial agents and antioxidants.

The cosmetic composition of this invention is a composition suitable for topical application to human skin, including leave-on and wash-off products. It is preferred that the compositions of the invention are leave-on compositions.

The compositions may be suitable packed in an appropriately sized packaging or dispenser. Packaging can be a jar or tube as well as any other format typically seen for cosmetic, cream, washing and lotion type products. The compositions may be applied topically and preferably 1 to 4 milligrams of composition is applied per square centimeter of skin.

Method and Use

The present invention also discloses use of the composite particles as obtainable by the process of the first aspect in a cosmetic composition for enhancing gloss of skin.

The present invention also discloses use of the composite particles as obtainable by the process of the first aspect in a cosmetic composition for hiding superficial imperfections of skin.

The present invention further discloses a method of enhancing gloss of skin comprising a step of applying thereto a cosmetic composition comprising the composite particles as obtainable by the process of the first aspect of the invention.

The present invention still further discloses a cosmetic method of hiding superficial imperfections of skin comprising a step of applying thereto a cosmetic composition comprising the composite particles as obtainable by the process of the first aspect of the invention.

The present invention also discloses use of composite particles as obtainable by the process of the first aspect in the manufacture of a cosmetic composition for enhancing gloss of skin.

The present invention yet further discloses use of composite particles of the first aspect as obtainable by the process in the manufacture of a cosmetic composition for hiding superficial imperfections of skin.

The following examples are provided to facilitate an understanding of the invention. The examples are not intended to limit the scope of the claims.

EXAMPLES

Example 1: Preparation of Composite Particles According to the Invention

The following materials were used:
(i) Silica sol having particle size of 50 nm
(j) N-(3-dimethylaminopropyl)-N'-ethylcarbodiimide hydrochloride (EDC)
(k) (3-aminopropyl) triethoxysilane (APETS)
(l) succinic anhydride (SA)
(m) N-hydroxysuccinimide (NHS)
(n) Dimethylformamide (DMF)
(o) Mica, with brand name Mica A® from JGC Corporation.

Step 1: Silanization of Silica (Silicon Dioxide) Nanoparticles

One (1) mL APTES was added dropwise into 10 ml of an ethanol dispersion of silica nanoparticles (0.1 g/mL) and stirred for two hours. The products were separated and washed by centrifugation. The amino-modified silica nanoparticles were collected as aqueous dispersion (0.1 g/mL) for further usage, and all reactions were taken under room temperature.

Step 2: Carboxylation of Mica Sheets

One (1) g ground mica was dispersed into 100 ml ethanol under stirring for 10 min to prepare mica dispersion, then 1 mL APTES was added drop by drop into the mica dispersion and stirred for another 2 hours. The products were separated and washed through centrifugation, resulted amino modified ground mica were then re-dispersed in DMF. 100 mg SA was added into the dispersion as powder, and the dispersion was then kept stirring for another 2 hours. The products were separated and washed through centrifugation, resulted carboxyl modified ground mica were collected as powders for further usage, and all reactions were taken under room temperature.

Step 3: Amidation Linking of Mica Sheets and Silica Nanoparticles

Five (5) g modified ground mica was dispersed into 8 ml DI water under stirring to prepare mica dispersion. Two (2) mL certain concentration of modified silica nanoparticles dispersion (500 mg/mL, 100 mg/mL, 50 mg/mL) was added into mica dispersion drop by drop. 200 mg EDC and 200 mg NHS were then added into the mixed dispersion as powder. The reaction underwent for two hours with stirring.

Various coverage of nanoparticles on sheets surface were achieved by adjusting the added amount of silica nanoparticles.

Analytical Method

Transmission electron microscopy (TEM) was performed on H-7650 (Hitachi, Japan) operated at an acceleration voltage of 100 kV. Scanning electron microscopy (SEM) was performed with a field emission scanning electron microanalyzer (Zeiss Supra 40) at an acceleration voltage of 5 kV. SEM images of composites were analyzed by Image J to estimate silica coverage on mica surface by the brightness contrast of silica and mica substrate.

Three different types of composite particles were prepared the process described hereinabove. Information about the particles is shown in Table 1.

Surface Coverage

Surface coverage is defined as the ratio of area covered by non-porous spherical particulate inorganic material to the area covered by the plate-like inorganic material.

Transmission electron microscopy (TEM) was performed on H-7650 (Hitachi, Japan) operated at an acceleration voltage of 100 kV. Scanning electron microscopy (SEM) was performed with a field emission scanning electron microanalyzer (Zeiss Supra 40) at an acceleration voltage of 5 kV. SEM images of the composites were analyzed by Image J to determine the surface coverage by the brightness contrast between silica and mica substrates.

The commercially available software named Image J (Version 1.51K) was used to measure the area(s). The procedure is detailed hereinbelow in a step-by-step manner.

Step 1 Open the SEM image via select File→Open samples→name of SEM file

Step 2 Covert the image to grayscale if not in grayscale: Image→Type→8-bit

Step 3 Sep measurement scale: draw a line over scale bar on the bottom of SEM image then Analyze→Set Scale. Draw a new line and confirm that the measurement scale is correct.

Step 4 Threshold new image of leaf using manual settings: Image→Adjust→Threshold and play with sliders to include all the spherical particles on the platelet in red and click "Apply". The manual threshold setting includes all the particle area.

Step 5 Calculate area of all spherical particles: enclose the analyzed area with the rectangular selection tool Analyze→Analyze Particles. In the window, toggle 'show outlines', check "Display Results", "Summary" and "Exclude on edges", then click 'OK'.

Outline of spherical particles is automatically drawn. And data window gives ratio of the % area, which is the surface coverage.

TABLE 1

| Low surface coverage composite particles | 3.5% silica and 96.5% mica | 24% coverage |
| Medium surface coverage composite particles | 4.7% silica and 95.3% mica | 34% coverage |
| High surface coverage composite particles | 19% silica and 81% mica | 76% coverage |

In the SEM images, silica appeared brighter than mica, due to poorer electrical conductivity of silica. So, the coverage of silica on mica could be equated to the proportion of the bright area. For the high surface coverage composite particle, the coverage reached as high as 76%. Further it was observed that all silica spheres formed a mono-layer on the surface of mica.

Example 2

The composites of Table 1 were formulated in a skincare composition. Basic details of the compositions are shown in Table 2 which needs to be read-with the cross-referenced contents of Table 3.

TABLE 2

| Phase | Ingredient | Wt % |
|---|---|---|
| Water phase | Water, to | 100% |
| | Composite/Particulate material | Refer Table 3 |
| | Tween ® 20 | 1 |
| | Glycerin | 2 |
| | VP/VA | 2 |
| Oil phase | Isopropyl myristate | 12 |
| Thickener | Simulgel ® EG | 3 |
| — | Total | 100 |

TABLE 3

| Ingredient/wt % | A | B | C | D | E |
|---|---|---|---|---|---|
| Water | 70 | 70 | 70 | 70 | 70 |
| Composite/Particulate material | 5% SS 1% 3H | 5% SS 2% 3H | 5% DC9509 3% 3H 0.5% CC6097 | 10% V640 | 10% S6 |
| Tween ® 20 | 1 | 1 | 1 | 1 | 1 |
| Glycerin | 2 | 2 | 2 | 2 | 2 |
| VP/VA | 2 | 2 | 2 | 2 | 2 |
| Isopropyl myristate | 12 | 12 | 12 | 12 | 12 |
| Simulgel ® EG | 3 | 3 | 3 | 3 | 3 |

| Ingredient/wt % | F | G | H | I | J |
|---|---|---|---|---|---|
| Water | 70 | 70 | 70 | 70 | 70 |
| Composite/Particulate material | 10% AR80 | 10% SS | 5% SS | 3% SS | 10% KII |
| Tween ® 20 | 1 | 1 | 1 | 1 | 1 |
| Glycerin | 2 | 2 | 2 | 2 | 2 |
| VP/VA | 2 | 2 | 2 | 2 | 2 |
| Isopropyl myristate | 12 | 12 | 12 | 12 | 12 |
| Simulgel ® EG | 3 | 3 | 3 | 3 | 3 |

| Ingredient/wt % | K | L | M | N | O |
|---|---|---|---|---|---|
| Water | 70 | 70 | 70 | 70 | 70 |
| Composite/Particulate material | 10% VA | 10% V310 | 10% S36 | 6% Mica A + 4% Cosmo55 | 6% Mica A + 4% AE1 |
| Tween ® 20 | 1 | 1 | 1 | 1 | 1 |
| Glycerin | 2 | 2 | 2 | 2 | 2 |
| VP/VA | 2 | 2 | 2 | 2 | 2 |
| Isopropyl myristate | 12 | 12 | 12 | 12 | 12 |
| Simulgel ® EG | 3 | 3 | 3 | 3 | 3 |

| Ingredient/wt % | P | Q | R | S | T |
|---|---|---|---|---|---|
| Water | 70 | 70 | 70 | 70 | 70 |
| Composite/Particulate material | 6% MearlmicaII + 4% Cosmo55 | 6% MearlmicaII + 4% Cosmo55 | 10% DC9509 + 1% TR-10 | 10% Low surface coverage particles | 10% Medium surface coverage particles |
| Tween ® 20 | 1 | 1 | 1 | 1 | 1 |
| Glycerin | 2 | 2 | 2 | 2 | 2 |
| VP/VA | 2 | 2 | 2 | 2 | 2 |
| Isopropyl myristate | 12 | 12 | 12 | 12 | 12 |
| Simulgel ® EG | 3 | 3 | 3 | 3 | 3 |

| Ingredient/wt % | U |
|---|---|
| Water | 70 |
| Composite/Particulate material | 10% High surface coverage particles |
| Tween ® 20 | 1 |
| Glycerin | 2 |

TABLE 3-continued

| | |
|---|---|
| VP/VA | 2 |
| Isopropyl myristate | 12 |
| Simulgel ® EG | 3 |

Note:
The following short forms have been used to represent certain commercially available materials that were tested.
SS: RonaFlair Softshade ® Ex. Merck, TiO$_2$ (33 to 41%)/SiCO$_2$ (28 to 34%) Mica (20-37%) Al$_2$O$_3$ (2 to 5%), Mica <15 µm.
3H: MSS-500/3H, KOBO, commercially available porous silica for blurring efficacy
CC6097 Momentive turbostratic boron nitride <5 µm
V640: Velvet Veil ® 640 Ex. JGC, 40% silica (600 nm) coated on Mica A
S6: Cashmir ® S6: JGC, 63.7% silica (600 nm) coated on Mica A
S3: Cashmir ® S3 Ex. JGC, 48% silica (300 nm) coated on Mica A
AR 80: Coverleaf ® AR-80 Ex., JGC, Talc:TiO$_2$:Al$_2$O$_3$:SiO$_2$ = 55:10:16:19
KII: Cashmir ® KII: JGC, 46.5% silica(300 nm) coated on Mica A
VA: Velvet Veil ® A Ex. JGC, ~8% silica(300 nm) coated on Mica A
V310: Velvet Veil ® 310 Ex. JGC, 10% silica (300 nm) coated on Mica A
A55: Cosmo ®55 Ex. JGC solid silica sphere, 600 nm
A250: AE1: 250 nm silica sphere
Mil: Mearlmica ® II Ex. BASF, Mica 35 µm
MCF Mearlmica ® CF Ex. BASF, Mica 25 µm
DC9509: Silicone elastomer particles Ex. Dow corning (63% active)
TR-10: Miyoshi Kasei Inc., 93% TiO$_2$, 4% Al$_2$O$_3$, 3% dimethicone, ~700 nm Example Ref. nos A and B contained a combination of two pigments, C contained three pigments/particles, compositions D to M contained a single commercially available composite particle, compositions N to Q contained a combination of commercially available composite particles, R contained a combination of particles and compositions S, T and U (all within the invention) contained composite particles according to the invention.

Blurring Index

This index is an indicator of the how good a composition is at concealing superficial imperfections of skin. Blurring Index (also called L&W Index) was measured by a 2-step process. In the first step, the gloss of artificial skin is measured before the application of any cosmetic composition.

Wrinkled Bio-Skin Plates (BP-EW1 #BSC, Beaulax Co., Ltd., Tokyo, Japan) made of polyurethane elastomer were used to mimic wrinkled human skin. Hereinafter they are abbreviated as BSP. A dual-polarized image system called SAMBA (Bossa Nova Technologies, USA) was used to measure the gloss of the BSP by following the method and principle described by Matsubara et. al., [*Skin Translucency: What Is It & How Is It Measured, The International Federation of Societies of Cosmetic Chemists (IFSCC) Congress* 2006, Osaka, Japan]. A software named SAMBA face system (Version 4.3) was used for the analysis. The BSP were tested against an incident light with exposure time of 80 milliseconds. Two operation modes were used—parallel polarization and crossed polarization. Thereafter, 28 mg of the concerned composition was applied thereon and it was spread by a finger cot in a circular area of 7 cm$^2$. The sample was left to dry for 30 minutes before being further tested. Thereafter, gloss was measured again as done before.

In the second step, the L&W (Line & Wrinkle) Index was determined as follows.

The incident light was reflected and scattered by BSP. The specular reflected light kept the same polarization as the incident light whereas the scattering light from the volume (diffused light) was un-polarized. The camera successively acquired two images corresponding to two states of polarization (parallel and crossed). The parallel image intensity (P) was contributed to by the reflected and the scattered light, and the crossed image intensity (C) was contributed to by the scattered light. The parallel image plus the crossed image is equal to the total image delivered by a conventional camera or perceived by human eye. The degree of gloss is as follows, (P−C)/(P+C). Thereafter, gloss of each pixel was calculated. The standard deviation (STD) of gloss is a measure of the uniformity of the skin appearance. The higher the deviation, the lower is the uniformity. The L&W index was calculated by the following equation:

(STD of gloss degree before applying sample minus STD of gloss degree after applying sample)/ (STD of gloss degree before applying sample).

The Index is directly proportional to efficacy of the composition at concealing superficial imperfections of skin. The data is presented in Table 4.

TABLE 4

| Example Ref. No. | Blur Index | % Increase in Gloss (th > 0.3) |
|---|---|---|
| A | 14.23 | 4.23 |
| B | 17.48 | 0.81 |
| C | 45.19 | −11.76 |
| D | 5.21 | 1.03 |
| E | 2.29 | 2.49 |
| F | 6.52 | −10.42 |
| G | −19.05 | 18.57 |
| H | −2.55 | 11.45 |
| I | −3.20 | 2.01 |
| J | −12.36 | 8.02 |
| K | −27.12 | 9.58 |
| L | −8.05 | 6.24 |
| M | −12.22 | 8.41 |
| N | −49.66 | 10.89 |
| O | −37.24 | 8.79 |
| P | −14.87 | 1.81 |
| Q | −16.98 | 6.25 |
| R | 4.36 | −8.58 |
| S | −15.74 | 11.68 |
| T | −6.06 | 5.65 |
| U | 6.70 | 3.08 |

Example reference number D, which is the composition comprising Velvet Veil® 640 40% silica (600 nm) coated on Mica A, shows the best performance as far as the Blur Index and gloss are concerned. However, the results indicate that performance of Examples S, T and U (all within the scope of this invention) was comparable to that of Example D and the amongst S, T and U, the composition U showed the best performance, i.e., high gloss and better ability to conceal superficial imperfections of skin as indicated the Blur Index. Composition U contained the high surface coverage composite particles comprising 19% silica and 81% mica, where the spherical material (silica) occupied 76% of the total surface area of the plate-like material (mica). On the other hand, V640 contained 40% silica (600 nm) coated on Mica A which formed the balance 60%.

The darker parts, like the valleys of wrinkled skin are dark because light does not reach the depth of the valleys. However the contrast between brighter parts and darker parts is more apparent in the case of compositions S, T and U. The increased blur index probably means increased and evenly bright pixels and the finer texture of skin can be better visible with an increase in the gloss.

The blur index and gloss obtained from compositions A and B were high enough but that was a result of a combination of ingredients/particles. From compositions E onwards to R, at least one of blur index or gloss was too low as compared to that offered by V640.

The invention claimed is:

1. A method of preparing composite particles comprising a non-porous spherical particulate inorganic material deposited on a plate-like inorganic material, where refractive index of said particulate inorganic material is greater than that of said plate-like inorganic particulate material, wherein, said spherical material occupies 20 to 80% of total surface area of said plate-like material and wherein the amount of said spherical material accounts for 2 to 20 wt % of said composite particles, further wherein said plate-like inorganic material is mica and said non-porous spherical particulate inorganic material is silicon dioxide, said method comprising the steps of:
  (i) silanization of said plate-like inorganic material to get a silanized material having functional groups "A";
  (ii) silanization of said non-porous spherical particulate inorganic material to get a silanized material having functional groups "B", where "A"≠"B"; and where said "A" and said "B" are capable of reacting with each other such that by way of their reaction, said non-porous spherical particulate inorganic material deposits on said plate-like inorganic material; and,
  (iii) reacting said silanized material having functional groups "A" with said silanized material having functional groups "B".

2. The method as claimed in claim 1, wherein "A" is carboxylic acid groups.

3. The method as claimed in claim 1, wherein "B" is amino groups.

4. The method as claimed in claim 1, wherein said non-porous spherical particulate inorganic material possesses a particle size ranging from about 50 to 1000 nm.

5. The method as claimed in claim 1, wherein said non-porous spherical particulate inorganic material is deposited as a monolayer on said plate-like inorganic material.

6. The method as claimed in claim 1, wherein said plate-like inorganic material possesses an average particle size ranging from about 10,000 to 30,000 nm.

7. The method as claimed in claim 1, wherein said plate-like inorganic material possesses a refractive index of at least 1.8.

8. The method as claimed in claim 1, wherein said plate-like inorganic material possesses a refractive index from 1.9 to 4.

9. A method of enhancing gloss of skin comprising a step of applying thereto a cosmetic composition comprising the composite particles as obtainable by the method as claimed in claim 1.

10. A cosmetic method of hiding superficial imperfections of skin comprising a step of applying thereto a cosmetic composition comprising the composite particles as obtainable by the method as claimed in claim 1.

11. The method as claimed in claim 1, wherein said non-porous spherical particulate inorganic material occupies 25 to 80% of the total surface area of said plate-like inorganic material.

12. The method as claimed in claim 1, wherein said mica is silanized by first reacting with (3-aminopropyl) triethoxysilane in an alcoholic medium followed by a reaction with succinic anhydride in dimethylformamide medium.

13. The method as claimed in claim 1, wherein said silicon dioxide is silianized by reacting with (3-aminopropyl) triethoxysilane in an alcoholic medium.

14. The method as claimed in claim 1, wherein said silanized material having functional groups "A" is reacted with the silanized material having functional groups "B" in the presence of (1-(3-dimethylaminopropyl)-3-ethylcarbodiimide) and N-hydroxysuccinimide.

15. The method as claimed in claim 1, wherein said plate-like inorganic material has a diameter of about 10 to 20 times greater than that of said non-porous spherical particulate inorganic material.

* * * * *